US012423539B2

(12) United States Patent
Koch

(10) Patent No.: US 12,423,539 B2
(45) Date of Patent: Sep. 23, 2025

(54) READING DEVICE FOR DETECTING A PLURALITY OF COMPUTER-READABLE CODES, READING SYSTEM AND METHOD FOR DETECTING A PLURALITY OF COMPUTER-READABLE CODES

(71) Applicant: Aesculap AG, Tuttlingen (DE)

(72) Inventor: Jan Koch, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/632,603

(22) Filed: Apr. 11, 2024

(65) Prior Publication Data
US 2024/0346271 A1 Oct. 17, 2024

(30) Foreign Application Priority Data
Apr. 12, 2023 (DE) ..................... 10 2023 109 249.9

(51) Int. Cl.
*G06K 7/14* (2006.01)
*G16H 40/40* (2018.01)
(52) U.S. Cl.
CPC ......... *G06K 7/1417* (2013.01); *G06K 7/1413* (2013.01); *G16H 40/40* (2018.01)
(58) Field of Classification Search
CPC .. G06K 7/1417; G06K 7/1413; G06K 7/0004; G16H 40/40
See application file for complete search history.

(56) References Cited

U.S. PATENT DOCUMENTS

| 9,477,976 | B2 | 10/2016 | Deck et al. |
| 2015/0370973 | A1* | 12/2015 | Jones ..................... G16H 20/17 705/2 |
| 2018/0114083 | A1 | 4/2018 | Richter et al. |

FOREIGN PATENT DOCUMENTS

| DE | 102021120340 A1 | 2/2023 |
| WO | 2008037094 A1 | 4/2008 |
| WO | 2016166379 A1 | 10/2016 |
| WO | 2022112606 A1 | 6/2022 |

* cited by examiner

*Primary Examiner* — Matthew Mikels
(74) *Attorney, Agent, or Firm* — Christopher A. Rothe; CM Law

(57) ABSTRACT

A reading device for capturing at least one computer-readable code of a medical product or a package of a medical product for assisting a user. The reading device includes a capturing device configured to capture an image of the medical product or its package with the at least one code and to extract product data contained in the code and an interpretation device configured to interpret the product data and to check whether predetermined product information is present in the product data. The reading device includes a code generating device configured to generate a result code from the product data.

19 Claims, 4 Drawing Sheets

READING DEVICE FOR DETECTING A PLURALITY OF COMPUTER-READABLE CODES, READING SYSTEM AND METHOD FOR DETECTING A PLURALITY OF COMPUTER-READABLE CODES

CROSS-REFERENCE TO RELATED APPLICATION(S)

This application claims priority under 35 U.S.C. § 119 to German Application No. 2023 109 249.9, filed on Apr. 12, 2023, the content of which is incorporated by reference herein in its entirety.

FIELD

The disclosure relates to a reading device, reading system, and method for capturing at least one computer-readable code of a medical product or a package of a medical product.

BACKGROUND

Tracking and documentation of medical devices used in connection with a patient or a medical procedure on a patient is essential in order to be able to trace the devices—whereby a device can also be any type of medical device—in the event of an infection or a device recall. It has to be possible to determine which specific items (medical devices), including their batch or serial number, have been used in connection with a patient, e.g. implanted or used. A lot number can sometimes also be referred to as a batch number.

Currently, manual documentation is common, where removable stickers are removed from the devices. Often these stickers are collected by staff in one way or another. For example, it is known that the stickers are attached to the gowns worn during the procedure. Later, at a workstation used for documentation, the stickers are removed and affixed to forms or paper, which can then be archived and/or digitized.

Two main standards have become established for medical devices, GS1 (Global Standards 1), e.g. GTIN (Global Trade Item Number), and HIBC (Health Industry Barcode). The Pharmacy Central Number (PZN) is also used for certain devices. In order to be able to assign the correct item to the scanned barcode, a database with master data of all items that may be used must be managed.

WO 2022/112606 A1 discloses a method for detecting several computer-readable codes, preferably barcodes and/or 2D codes, of a medical product or packaging of a medical product to assist a user, as well as a corresponding reading device and reading system.

A disadvantage of known systems for capturing codes from medical products is that it is not possible to transmit them to predefined database systems, in particular hospital information systems (HIS), as these only accept predefined data formats. It is known to use barcode scanners, but these can only send one code at a time and are designed to only send data to a single system.

SUMMARY

The disclosure is therefore based on the object of providing a reading device with improved data transmission. Furthermore, a corresponding reading system and a corresponding method are to be specified.

With respect to the reading device, the above object is solved according to the disclosure by a reading device for capturing at least one computer-readable code of a medical product or a package of a medical product for assisting a user, wherein the reading device comprises a capturing device configured to capture an image of the medical product or its package with the at least one code and to extract the product data contained in the code, and wherein the reading device comprises an interpretation device configured to interpret said product data and to check whether predetermined product information is present in the product data, and wherein the reading device comprises a code generation device configured to generate a result code from the product data.

The disclosure is based on the consideration that it is useful or necessary to transmit the corresponding data to external systems, in particular the respective hospital information system (HIS), when recording codes of medical products. However, the HIS usually has a specific and possibly proprietary interface, so that it is not easily possible to transmit the recorded data from a reading device to the HIS.

As has now been recognized, these requirements can be met by the reading device comprising a code generation device that generates a common code from the captured code(s), which can then be transmitted to the HIS. In this way, a common code that can be processed by the HIS is generated from data consisting of one or more codes, which may have different formats. The reading device is thereby enabled to transmit this code to the external system.

Advantageously, the code generation device is configured to generate a common result code from all interpreted product data. This ensures that all recorded product information is summarized in a common code.

Capturing or scanning the image is preferably understood to mean that the user or a device photographs the medical device or the packaging of the medical device, preferably with a camera, e.g. a camera of a desktop device or smartphone camera, or scans the product or the packaging with a capturing device, e.g. a camera. Product information is preferably understood to be information relating to the medical device and advantageously includes the product ID, an expiry date and a batch number. The product information may also contain further information about the medical device, such as a maximum transportation or storage time for a vaccine.

Interpretation of the code data means retrieving information from the computer-readable codes. For example, a code can be interpreted to identify it as a GS1 standard code that contains the product ID. The product ID is a number or a combination of numbers and letters that can be read or extracted from the code. The code, for example a barcode, contains data, for example the numbers encoded by the bars. The corresponding product information is then obtained after interpreting the data, for example, after recognizing the data format, the result is a product ID.

The capturing device is preferably configured to recognize codes of the Global Standards 1 (GS1), Health Industry Bar Code (HIBC), and Pharmacy Central Number (PZN) standards and to extract the encoded data.

The code generation device preferably generates the result code by sequentially stringing together the product data of all interpreted codes. In particular, a common string, i.e. a character string containing all product data, is generated.

The result code is preferably a barcode. This makes it possible to transmit the result code to an HIS with an interface that only accepts barcodes. Data matrix codes are preferred. If the information is contained in several barcodes/codes, the multireader assembles information from several codes as one character string. The sequence should then be Jan. 17, 2010 for LOT or Jan. 17, 2021 for SN, whereby the numbers 17 and 21 stand for identifiers of the corresponding barcode.

The detection device is advantageously designed to detect barcodes and/or data matrix codes. The advantages of data matrix codes are, in particular, that they require little space and can also be read if approx. 30% of the data matrix code is damaged.

In an advantageous embodiment, the reading device comprises a transmission device with an interface for transmitting the result code to a hospital information system, wherein the transmission device is designed to transmit the result code to the hospital information system.

The interface is advantageously designed as an MDM interface according to the HL7 standard In a preferred embodiment, the reading device is configured to determine, based on the product information extracted from the product data, whether a predefined set of relevant information for the medical product is contained in the product information of the at least one detected code and/or in a linked database stored in a storage unit of the reading device and/or in a storage unit of a server.

A predefined set of relevant information is a set of information that relates to the medical device that needs to be scanned and documented. The predefined relevant information can be defined, for example, by legal requirements, by the user or by different requirements such as internal hospital requirements.

The interpretation device is preferably designed to transmit the product information to the database when the result code is transmitted to the hospital information system. In this way, it can be ensured that the database of data is kept up to date.

The interpretation device is advantageously configured to compare the product information from the at least one code with product information in the database and to store the product information from the at least one code in the database if the product information was not stored in the database.

The database, which for example is set up in the cloud, can know requirements for the documentation obligation of a product, for example: subject to batch management (yes/no), subject to serial number management (yes/no), subject to expiry date management (yes/no). If a product or article does not require any further data, it is sufficient to identify the product; this can preferably be done using EAN 8, EAN 13, GS1-GTIN, PZN. In many cases, all the required information is encoded in a machine-readable code. The GS1 provides the following identifiers for this:

(01)—GTIN=trade number; (10)—batch; (21)—serial number; (17)—expiry date.

The interpretation device is advantageously configured, when acquiring a plurality of codes, to select one code as a relevant code if the product data of the at least one other code is fully contained in the code data of that code, and to select two or more codes as relevant codes if the product data is not contained in other codes, and wherein the code generation device is configured to form the result code from product data of the code or codes selected as relevant. The computer-readable code(s) is/are thus selected as relevant code(s) if it/they contains the predefined amount of relevant information. The relevant code(s) may be a single code containing all the relevant information or a set of codes containing the relevant information combined.

In a preferred embodiment, the reading device comprises a display device which is configured to display an overlay image with the at least detected code image and visual information. The display device is advantageously designed as a touch display or comprises a touch display. This also enables areas of the touch display to be used as an input device for the input of data by the user.

The visual information preferably comprises at least one colored marking. In this way, the visual information is directly visible to the user. The colored marking is preferably displayed at least partially transparently on or overlapping with the respective detected code in order to facilitate its assignment to the respective code by the user.

The color of the at least one colored marking is advantageously dependent on the type and/or amount of product information.

In a preferred embodiment, the display device comprises a display panel for instructions to the user.

In a preferred embodiment, the reading device comprises an input device for entering information by the user. The user can use the input device, for example, to confirm or cancel processes or make manual data entries.

If the product is known/unknown and the information is complete, it is preferable to send it directly to the HIS without prior confirmation. If the product is known and the information is incomplete, either additional codes are recognized (complete transmission without confirmation), or the user confirms and completes missing data, e.g. on the touch screen. If the product is unknown and the information is incomplete, it requires interpretation by the user as to which information is to be documented for this product, in particular Batch (yes/no)
Serial number (yes/no)
Expiry date (yes/no).

The product information preferably includes the product ID and/or an expiry date and/or a batch number.

In a preferred embodiment, the reading device is designed as a desktop device for stationary use.

Preferably, the reading device comprises an illumination unit for illuminating the codes to be detected.

In an alternative preferred embodiment, the reading device is designed as a mobile device, in particular a smartphone or tablet.

The detection device, the interpretation device, the display device and the code generation device can be implemented in the reading device on the hardware and/or software side.

In summary, the reading device according to the disclosure comprises a plurality of devices, the respective function and interaction of which with the other devices is briefly described. The capturing device can scan one or more computer-readable codes such as barcodes or 2D codes (in particular data matrix codes). The capturing device identifies the computer-readable codes in the captured image and transmits the product data, i.e. the data encoded with the aid of the codes, in particular numbers, of the multiple codes from the capturing device to the interpretation device, which retrieves the product information from the product data. The product information is information relating to the medical device, e.g. the product identifier, the batch number and the expiry date of the medical device.

The interpretation device determines whether the predefined relevant information is contained in the product information of the relevant codes. The interpretation device also preferably checks whether missing product information is stored in the database.

The interpretation device or evaluation device selects one code as the relevant code if all the product information of the other codes is also contained in this one code. If there is not one code that contains all the product information of the other codes, several codes can be the relevant codes. A relevant code is any code that contains new product information. So if several codes are relevant, the information contained in the codes combines the predefined set of relevant information.

The retrieved product information is preferably stored in the (master data) database by the reading device. The evaluation device preferably checks whether the product information of the captured product contains the predefined relevant information or whether the predefined relevant information can be retrieved from the database instead. It is possible to combine the product information from the code data and the product information retrieved from the database to obtain the predefined relevant information. The code generation device generates a code that is suitable for transmission to the HIS.

With respect to the reading system, the above task is solved according to the disclosure by a reading system for detecting a plurality of computer-readable codes of a medical device or a package of a medical device to assist a user, thereby comprising at least one reading device described above as a client device, further comprising a central server having a memory with a database, wherein the server is connected to the at least one reading device to transfer data to and from the reading device.

The interface of the transmission device and/or the interface to the server can be either wired or wireless. With a wireless interface, the data is sent wirelessly to the HIS. The data does not necessarily have to be sent live. The data could be collected in the mobile device and then successively sent to the HIS in a processing procedure.

With regard to the method, the above task is solved in accordance with the disclosure with a first step, namely capturing an image of the medical product or its packaging with the codes by a capturing device with a camera. In a second step, at least one code is extracted from the captured image and the product data encoded therein and it is checked whether predetermined product information is present in the product data. In a third step, the product data is interpreted and at least one piece of product information is retrieved from the product data, and in a fourth step, a result code is generated from at least one piece of product information of an interpreted code.

Advantageously, the result code is transmitted to an external system, in particular a hospital information system.

The result code is preferably generated by sequentially lining up the product data of all interpreted codes.

The disclosure also relates to a computer-readable storage medium having instructions which, when executed by a computer, cause the computer to perform the method described above.

The advantages of the disclosure lie in particular in the fact that the reading device can capture several codes simultaneously and create a common result code or summarizing code from the data contained therein, which is transmitted to an external system, in particular in HIS.

From a set of several computer-readable codes, the best code for the user is highlighted and additional information is provided. Thus, the user knows exactly which code from a set of codes is the best available code. If there is not a single code on the medical device or packaging that contains all the relevant information, the product information from multiple codes can be combined to collect the relevant information.

By providing the user with feedback on whether or not the individual code contains all the relevant information, the reordering of medical devices to replenish stock to a predetermined number of items can be easily automated by ensuring that the information system has accurate usage information in real time.

BRIEF DESCRIPTION OF THE DRAWINGS

An embodiment of the disclosure is explained in more detail in connection with the following drawing figures, which show highly schematized representations.

Identical parts are marked with the same reference signs in all figures.

DETAILED DESCRIPTION

Figure 1:
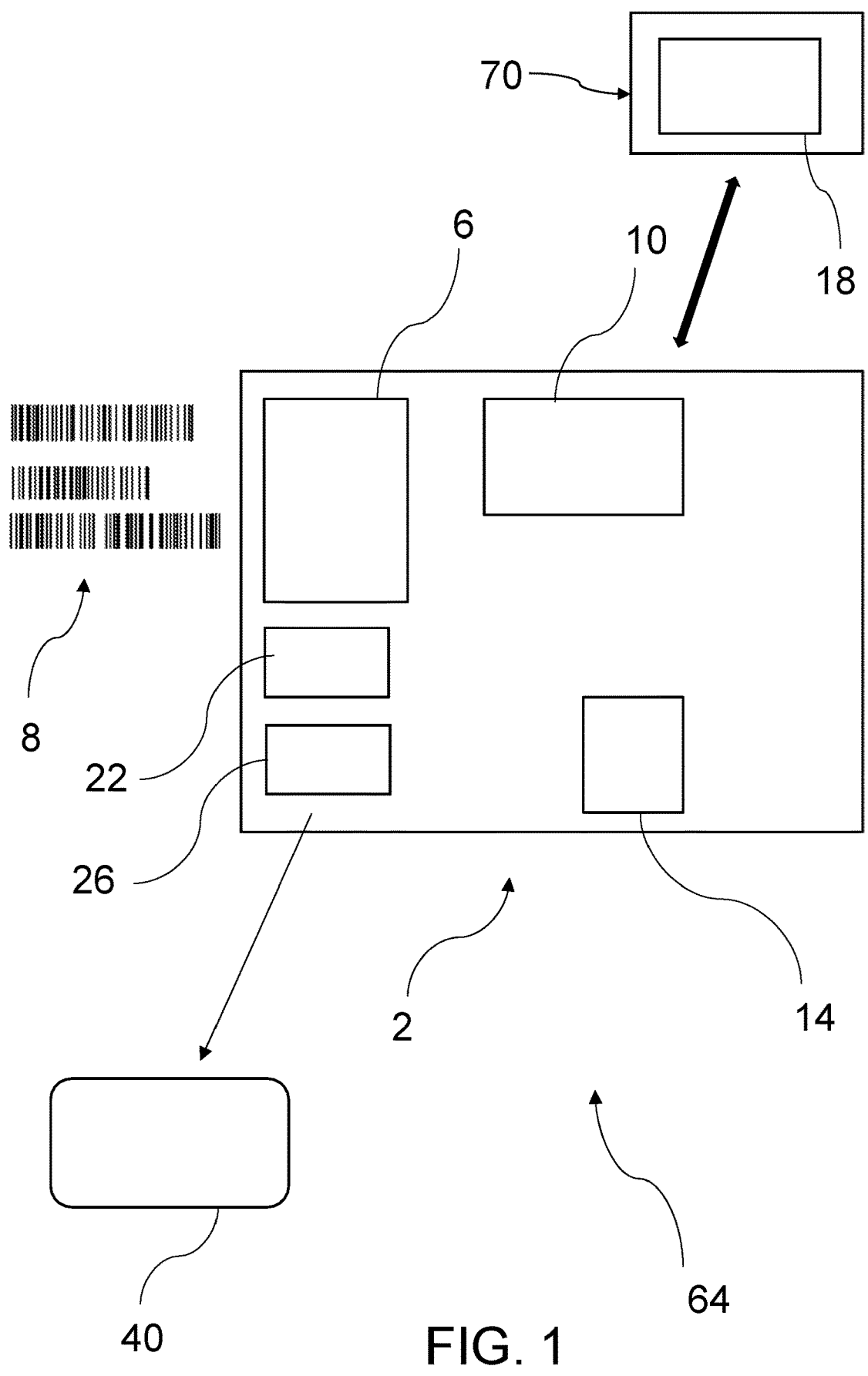
FIG. 1 shows a reading device in a preferred embodiment.

FIG. 1 shows a schematic view of a reading device 2 according to a preferred embodiment. The reading device 2 comprises a capturing device 6, an interpretation device 10, a display device 14, a database 18, a code generating device 22 and a transmission device 26.

The capturing device 6 is preferably designed as a camera, whereby the reading device 2 is in this case designed as a smartphone. In another preferred embodiment, the reading device 2 is designed as a device which is designed for stationary use at the documentation workstation of a hospital information system and has a camera.

The user uses the capturing device 6 to capture an image of a set of barcodes or other types of codes 8 or to scan the set of codes. The codes 8, which in the illustrated embodiment example are in the form of barcodes, are extracted from the captured image or recognized in the captured image.

The interpretation device 10 or evaluation device decodes codes, resulting in product data, and recognizes which product information is stored in the product data of the individual codes 8. The interpretation device 10 then determines whether the predefined amount of relevant information is present in the barcodes or in a linked database 18. The interpretation device 10 selects the relevant codes and highlights the relevant codes on the display device 14. The database 18 may be implemented within the reading device 2 or, as shown, may be external to it.

The code generating device 22 generates a result code from at least one of the codes recognized by the interpretation device 10, in particular from all codes, which in the present case is designed as a barcode and has the format of a string, i.e. a character string.

The reading device 2 comprises a transmission device 26 or transmission unit with an interface to a hospital information system 40. It transmits the result code to the hospital information system 40.

FIG. 1 also shows a reading system 64, which comprises the reading device 2 as a client. The database 18 shown in the figure is part of a central server 70 having a memory with the database 18, the server 70 being connected to the at least one reading device 2 to transfer data to and from the reading device 2.

Figure 2:
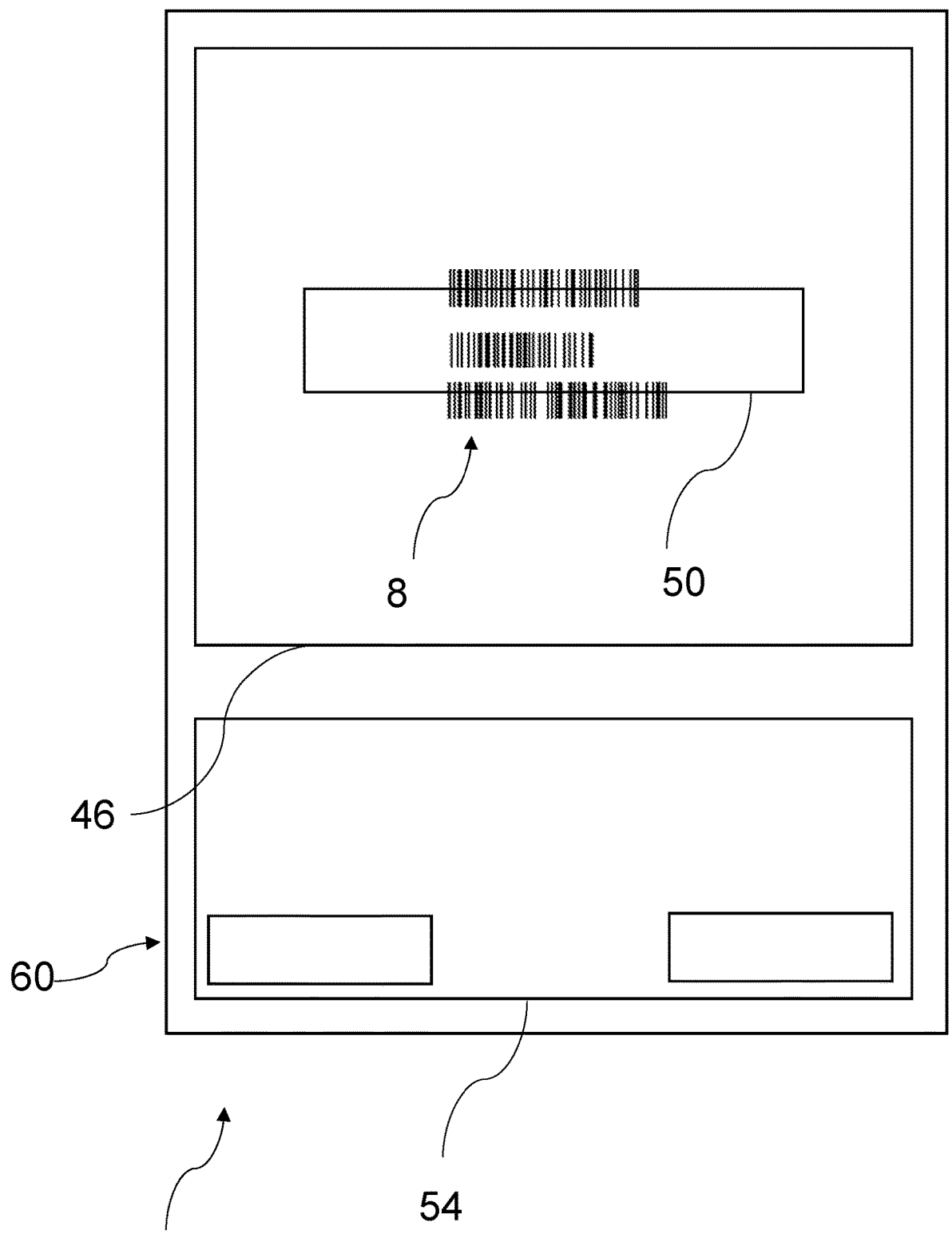
FIG. 2 shows a display device of the reading device according to FIG. 1.

In FIG. 2, the display device 14 of the reading device 2 according to FIG. 1 is shown enlarged. The display device 14 has an overlapping area 46 in which the camera image of the code 8 is displayed, with a marker 50 being displayed above the code 8. The marker 50 is displayed at least partially overlapping with the code 8. This allows the user to assign the marker 50 to the code 8. Such an assignment is particularly useful when several markers are detected at the same time. The marker is preferably displayed as an at least partially transparent, in particular rectangular, field, which is also referred to below as a "brush".

The display device 14 has an information area 54. In this information area 54, the product information extracted by the interpretation device 10 from the data encoded in the code 8 is displayed. In this way, the user receives immediate feedback on the information extracted from the codes. Preferably, the product information is displayed next to symbols or icons so that the user can immediately recognize which product information has been extracted.

The interpretation device 10 is configured to validate the product information and the display device 14 is configured to display corresponding messages in the information area 54. Preferably, the display device indicates in the information area 54 when the expiration date has passed.

The display device 14 has an input device 60 that accepts input from the user. In the preferred embodiment example, the display device 14 is designed as a touch display, wherein the input device 60 is designed as operating elements superimposed on the touch display.

If the expiry date has passed, two control elements are displayed with the labels "Use" and "Do not use". When communicating with the HIS, the character string is sent to the HIS as a string. This corresponds to the case in which the user would operate a barcode scanner/keyboard barcode scanner. The preferred interface is USB.

A green marker or "brush" is used if the article is known, especially if there is no obligation to document the batch, serial number or expiry date (or the article is subject to batch/serial number requirements and the production information has also been processed). If the complete information is extracted from two codes, a marker is displayed on both codes.

A yellow marker is used if the recognized information is incomplete. If, for example, only the product has been recognized, the batch and expiry date are recorded automatically or the missing information is added manually by entering it in the input device 60. If, for example, only one of the two codes has been recorded, a yellow "brush" indicates that the information is incomplete. If only the batch/expiry date have been scanned, the product is unknown. If only the product was scanned, but the item has a batch or serial number requirement, the production is unknown. The brush is preferably an online overlay via the live stream of the camera.

Missing information such as expiry date, batch, serial number can be entered manually on the touchscreen (keyboard shown on display).

The reading device 2 checks whether an article becomes known by communicating with the database 18 (i.e. in particular the HIS in the cloud).

Two basic approaches can be taken to achieve the objective of the multi-reader with interface to the HIS:

Master data must be known in the HIS.
Master data must be known in the HIS and in the cloud.

The product data extracted from the codes is preferred as extracted (1:1) to the HIS, regardless of whether the product information is stored in the database 18. The corresponding product information is fed into the database 18 by the reading device 2.

In a preferred embodiment, when scanning an EAN13/a GTIN for the first time, the user is asked by a message displayed in the information area 54 whether the product is a product requiring documentation (for which the customer wishes to document the batch, serial number or expiry date). The user can confirm this and enter the missing information using the corresponding input fields in the input device 60, or the packaging contains additional codes.

In the event that the reading device 2 recognizes that at least one code is missing or damaged and not all the necessary information can be extracted from the codes, the information area 54 signals to the user that manual input of the missing information is necessary. The user can confirm this in the input device 60. A pop-up can be displayed in the display device 14 for this purpose. A virtual keyboard is displayed in the input device 60 for manual input of missing information.

In the event that codes with a non-standardized format are captured by the capturing device 6, a message is displayed to the user in the information area 54 indicating that the product information must be captured manually. If necessary, a virtual keyboard is displayed in the input device 60 for this purpose. The codes are superimposed with orange markers.

In further embodiments, a mechanical keyboard can be provided for entering product information.

The reading device 2 is preferably configured to display and/or modify and/or delete product information contained in the database 18.

Figure 3:
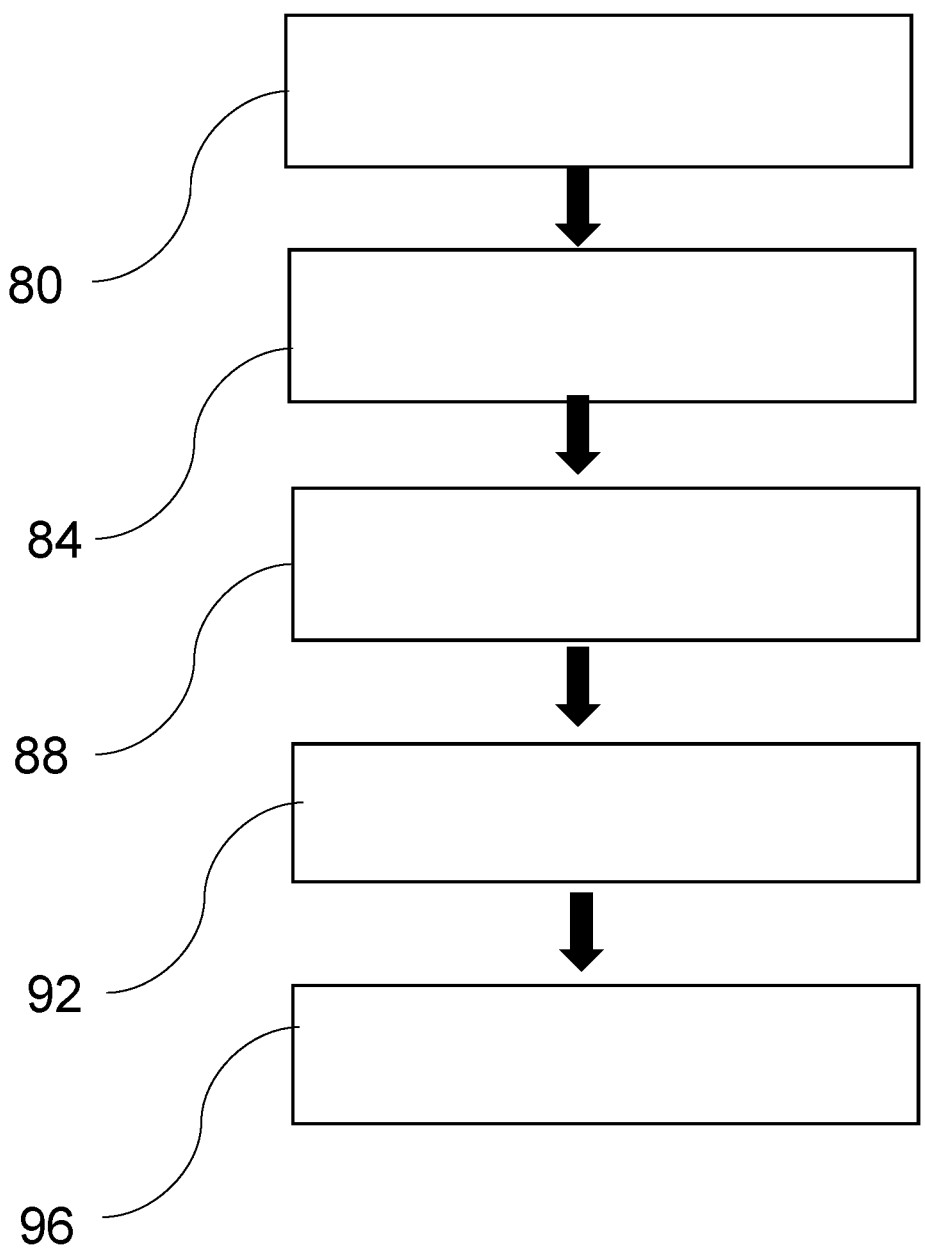
FIG. 3 shows a flowchart of a method according to a preferred embodiment.

In FIG. 3, a flowchart of a method for capturing a plurality of computer readable codes, preferably barcodes and/or 2D codes, of a medical device or packaging of a medical device to assist a user is shown.

In a first step 80 of the method, an image of a medical device or its packaging with the codes is recorded by a recording device with a camera. The recording device may be a smartphone or a desktop device with a camera. In a second step 84 following step 80, at least one code in the captured image is extracted and the product data encoded in the code is extracted.

In a third step 88 following step 84, at least one piece of product information is retrieved from the product data. A check is made as to whether predefined product information is present in the product data, In a step 92 following step 88, a result code is generated from at least one product information of an interpreted code. In a subsequent step 96, the result code is transmitted to a hospital information system.

The process is implemented in software and/or hardware, for example in a desktop computer with a camera or a smartphone.

Figure 4:
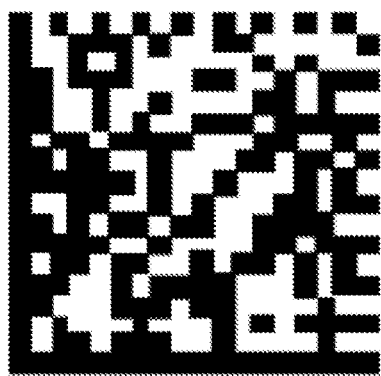
FIG. 4 shows an exemplary two-dimensional data matrix code.
Figure 5:
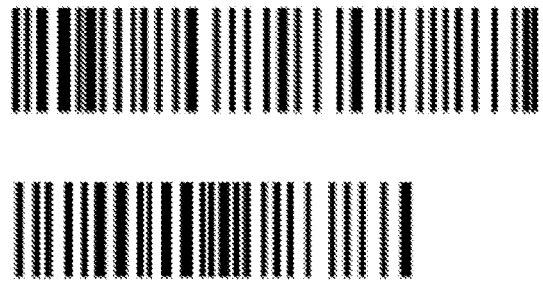
FIG. 5 shows two exemplary barcodes.
Figure 6:
FIG. 6 shows two exemplary barcodes with character strings.
Figure 7:
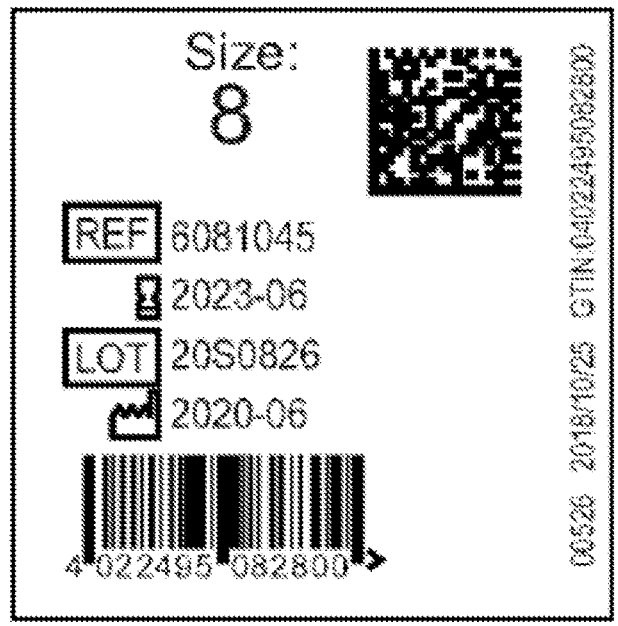
FIG. 7 shows an exemplary section of a package with a data matrix code and a barcode.

Examples of codes that can be processed by the reading device 2 or with the aid of the method are shown in FIGS. 4 to 7. An example data matrix code is shown in FIG. 4. FIG. 5 shows two barcodes arranged one above the other. FIG. 6 shows two codes arranged one above the other, whereby the coded information is additionally indicated by means of alphanumeric characters. FIG. 7 shows an example of packaging for a medical device which contains a barcode and a data matrix code. For further examples of codes and arrangements of codes, reference is made to WO 2022/112606 A1 already cited in the introductory section.

LIST OF REFERENCE SIGNS 2 reading device
6 capturing device
8 codes
10 interpretation device
14 display device
18 database
22 code generating device
26 transmission device
40 hospital information system
46 overlapping area
50 marker
54 information area
60 input device
64 reading system
70 server
80 step
84 step
88 step
92 step
96 step

The invention claimed is:

1. A reading device for detecting at least one code of a medical device or a package of a medical device to assist a user, the at least one code being computer-readable, the reading device comprising:
   a capturing device configured to capture an image of the medical device or the package of the medical device and to extract product data contained in the at least one code;
   an interpretation device configured to interpret the product data and to check whether predetermined product information is present in the product data;
   a code generating device configured to generate a result code from the product data; and
   a transmission device with an interface for transmitting the result code to a hospital information system, wherein the transmission device is designed to transmit the result code to the hospital information system;
   wherein the interpretation device is configured to determine, based on the product data extracted from the product data, whether a predefined set of relevant information for the medical device is contained in the product data of the at least one code and/or in a linked database stored in a storage unit of the reading device and/or in a storage unit of a server.

2. The reading device according to claim 1, wherein the code generating device is configured to generate the result code in a format accepted by the hospital information system.

3. The reading device according to claim 1, wherein the at least one code comprises a plurality of codes and the code generating device generates the result code by sequentially lining up the product data of all of the plurality of codes.

4. The reading device according to claim 1, wherein the result code is a barcode and/or a data matrix code.

5. The reading device according to claim 4, wherein the reading device is configured to present the barcode and/or the data matrix code in a format readable by the hospital information system.

6. The reading device according to claim 1, wherein the interface is designed as an MDM interface according to standard HL7.

7. The reading device according to claim 1, wherein the interpretation device is designed to transmit the product data to the linked database when the result code is transmitted to the hospital information system.

8. The reading device according to claim 7, wherein the interpretation device is configured to match the product data from the at least one code with product information in the linked database and to store the product information from the at least one code in the linked database when the product information was not stored in the linked database.

9. The reading device according to claim 1, wherein the capturing device is designed to detect barcodes and/or data matrix codes.

10. The reading device according to claim 1, wherein the interpretation device, when detecting a plurality of codes comprising at least a first code and a second code, is configured to select the first code as a relevant code when the product data of at least the second code is fully included in code data of the second code, and to select at least the first code and the second code as relevant codes when the product data is not included in other codes, and wherein the code generating device is configured to form the result code from product data of the relevant code or relevant codes.

11. The reading device according to claim 1, further comprising a display device configured to display an overlay image containing the at least one code and visual information.

12. The reading device according to claim 1, wherein the reading device is designed as a desktop device for stationary use.

13. The reading device according to claim 12, further comprising an illumination unit for illuminating the at least one code.

14. The reading device according to claim 1, wherein the reading device is designed as a mobile device.

15. A reading system for detecting a plurality of computer-readable codes of a medical device or a package of the medical device for assisting a user, the reading system comprising:
   at least one reading device according to claim 1 as a client device; and
   a central server having a memory with a database,
   the server being connected to the at least one reading device for transferring data to and from the at least one reading device.

16. A computer-implemented method for capturing a plurality of codes of a medical device or a package of the medical device to assist a user, the plurality of codes being computer-readable, the computer-implemented method comprising:
   recording an image of the medical device or the package using a reading device with a camera;
   extracting at least one code in the image, and extracting product data encoded in the at least one code;
   interpreting the product data and retrieving at least one piece of product information from the product data and checking whether specified product information is available in the product data; and
   generating a result code from the at least one piece of product information of the at least one code;
   determining, based on the product information extracted from the product data, whether a predefined set of relevant information for the medical device is contained in the product information of the at least one code and/or in a linked database stored in a storage unit of the reading device and/or in a storage unit of a server; and transmitting the result code to an external system.

17. The computer-implemented method according to claim 16, wherein the external system is a hospital information system.

18. The computer-implemented method according to claim 16, wherein the at least one code comprises a plurality of codes and the result code is generated by sequentially lining up the product data of all of the plurality of codes.

19. A computer readable storage medium comprising instructions which, when executed by a computer, cause the computer to perform the steps of claim 16.

* * * * *